(12) United States Patent
Liang et al.

(10) Patent No.: US 11,779,672 B2
(45) Date of Patent: Oct. 10, 2023

(54) CONTROL METHOD OF INTELLIGENT STERILITY TEST PUMP, STERILIZATION METHOD AND APPLICATION THEREOF

(71) Applicant: JIANGSU SUJING GROUP CO., LTD., Jiangsu (CN)

(72) Inventors: Fengfei Liang, Jiangsu (CN); Jiyong Sun, Jiangsu (CN); Weidong Shen, Jiangsu (CN); Jian Chen, Jiangsu (CN)

(73) Assignee: JIANGSU SUJING GROUP CO., LTD., Jiangsu (CN)

( * ) Notice: Subject to any disclaimer, the term of this patent is extended or adjusted under 35 U.S.C. 154(b) by 0 days.

(21) Appl. No.: 17/907,082

(22) PCT Filed: Dec. 11, 2020

(86) PCT No.: PCT/CN2020/135677
§ 371 (c)(1),
(2) Date: Sep. 22, 2022

(87) PCT Pub. No.: WO2022/082968
PCT Pub. Date: Apr. 28, 2022

(65) Prior Publication Data
US 2023/0256127 A1 Aug. 17, 2023

(30) Foreign Application Priority Data
Oct. 19, 2020 (CN) .......................... 202011116805.4

(51) Int. Cl.
*A61L 2/28* (2006.01)
*A61L 2/03* (2006.01)
*A61L 2/00* (2006.01)

(52) U.S. Cl.
CPC ............... *A61L 2/28* (2013.01); *A61L 2/0005* (2013.01); *A61L 2/03* (2013.01); *A61L 2202/21* (2013.01)

(58) Field of Classification Search
CPC ............. A61L 2/28; A61L 2/0005; A61L 2/03
(Continued)

(56) References Cited

U.S. PATENT DOCUMENTS

| | | | | |
|---|---|---|---|---|
| 2005/0221417 | A1* | 10/2005 | Houghton | ............... C12Q 1/22 435/287.1 |
| 2010/0193413 | A1* | 8/2010 | Lendenfeld | ............ C12M 41/38 210/85 |

(Continued)

FOREIGN PATENT DOCUMENTS

| | | |
|---|---|---|
| CN | 2393886 Y | 8/2000 |
| CN | 108119345 A | 6/2018 |

(Continued)

OTHER PUBLICATIONS

Chinese Office Action issued for Chinese Patent Application No. 202011116805.4, dated Sep. 23, 2021 in 15 pages including English translation.

(Continued)

*Primary Examiner* — Arlen Soderquist
(74) *Attorney, Agent, or Firm* — Knobbe, Martens, Olson & Bear, LLP

(57) ABSTRACT

A control method of an intelligent sterility test pump, a sterilization method and its application. The control method includes monitoring the real-time current of a DC drive motor through a current detection module, to adjust the rotating linear velocity of a peristaltic pump head in real time; when the peristaltic pump head is in a state of pushing a liquid to be tested, reducing the rotating linear velocity of the peristaltic pump head; and when the peristaltic pump head is in an idling state, increasing the rotating linear velocity of the peristaltic pump head. A sterilization method includes the control method of the intelligent sterility test (Continued)

pump. Application of the sterilization method in preparation or detection of foods and medicines.

5 Claims, 3 Drawing Sheets

(58) Field of Classification Search
USPC .............................................................. 436/1
See application file for complete search history.

(56) References Cited

U.S. PATENT DOCUMENTS

| | | | |
|---|---|---|---|
| 2013/0109052 A1* | 5/2013 | Yan | C12Q 1/22 435/297.2 |
| 2013/0280104 A1 | 10/2013 | Heide et al. | |
| 2015/0192505 A1* | 7/2015 | Okanojo | G01N 1/4077 435/309.1 |

FOREIGN PATENT DOCUMENTS

| | | | |
|---|---|---|---|
| CN | 210290088 U | 4/2020 | |
| CN | 111254068 A | 6/2020 | |
| CN | 111366517 A | 7/2020 | |
| CN | 111779655 A | 10/2020 | |
| DE | 102009048790 B4 * | 7/2015 | ......... B01D 46/0086 |
| EP | 3696412 A1 | 8/2020 | |

OTHER PUBLICATIONS

International Search Report and Written Opinion issued for International Patent Application No. PCT/CN2020/135677, dated Jul. 19, 2021 in 14 pages including English translation.

* cited by examiner

CONTROL METHOD OF INTELLIGENT STERILITY TEST PUMP, STERILIZATION METHOD AND APPLICATION THEREOF

CROSS-REFERENCE TO RELATED APPLICATIONS

This application is a U.S. National Phase under 35 U.S.C. § 371 of International Application PCT/CN2020/135677, filed Dec. 11, 2020, which claims priority from Chinese Patent Application No. 202011116805.4 filed with the China Patent Office on Oct. 19, 2020, each of which is incorporated herein by reference in its entirety.

TECHNICAL FIELD

The present disclosure relates to an intelligent sterility test pump, in particular to a control method of an intelligent sterility test pump, and a sterilization method and its application.

BACKGROUND

In the current social production process, especially in the pharmaceutical, food and other industries, the requirements for sterility are getting higher and higher, and the bacteria collector is the main instrument used at home and abroad to collect the bacteria that may exist in the liquid to be tested. It transfers the liquid to be tested from the original packaging of the liquid to the collection bottle without contact through a peristaltic pump, and collects bacteria by filtering the liquid to be tested through the filter paper in the collection bottle. In the whole test process, the integrity of the filter membrane is a key indicator that affects the effective detection rate, therefore, the integrity of the filter membrane must be tested before and after the test, and if the filter membrane is found to be damaged after the test, the test is invalid. However, if the filter membrane is damaged during the detection process and cannot be known in advance, it can only be known after the filter membrane is taken out after the detection is completed, the existence of these problems is not conducive to improving the detection efficiency, therefore, ensuring the integrity of the filter membrane during the detection process is a technical problem to be solved urgently by those skilled in the art.

For example, Chinese invention patent CN111366517A discloses an intelligent sterility test pump and a control method thereof. The intelligent sterility test pump includes a base, a support rod arranged on the base, and a liquid holder arranged on the upper end of the support rod, a peristaltic pump assembly arranged on the base, a collection bottle holder and a display, the peristaltic pump assembly includes a peristaltic pump head, a DC (direct current) drive motor for driving the peristaltic pump head, a motor drive module providing current for the DC drive motor, a current detection module that detects the magnitude of the current passing through the DC drive motor, and a control module that issues a prompt message through the display when the current detection module detects a change in the magnitude of the current passing through the DC drive motor; the control method adopts the above-mentioned intelligent sterility test pump, and when the current detection module detects that the current passing through the DC drive motor becomes larger, a filter membrane clogging prompt is sent, and when the current detection module detects that the current passing through the DC drive motor becomes smaller, a filter membrane damage prompt is sent. This patent can only obtain the information in time after the filter membrane is damaged, and then interrupt the detection, and replace the filter membrane to improve the detection efficiency, but it does not improve the integrity of the filter membrane during the detection process.

SUMMARY

The purposes of the present disclosure are to overcome the deficiencies of the prior art, and to provide an improved control method of an intelligent sterility test pump, wherein the control method can achieve the stability of controlling the pressure in a collection bottle, ensure the integrity of a filter membrane in the collection bottle, prevent the leakage of the filter membrane caused by pressure pulse, reduce invalid detection, and improve the detection efficiency.

The present disclosure further provides a sterilization method comprising the above control method of the intelligent sterility test pump.

The present disclosure further provides application of a sterilization method in preparation or detection of foods and medicines.

To achieve the above purpose, the technical solution employed by the present disclosure is:

A control method of an intelligent sterility test pump, the intelligent sterility test pump comprises a base, a support rod arranged on the base, and a liquid holder arranged on an upper end of the support rod, a peristaltic pump assembly arranged on the base, a collection bottle holder and a display, the peristaltic pump assembly comprises a peristaltic pump head, a DC (direct current) drive motor for driving the peristaltic pump head, a motor drive module providing current for the DC drive motor, a current detection module that detects the magnitude of the current passing through the DC drive motor, and a control module, the peristaltic pump head comprises a pump shaft and a plurality of rollers rotatably arranged on the pump shaft, and roller gaps being formed between two adjacent rollers; wherein, the peristaltic pump head comprises a state of pushing a liquid to be tested and an idling state of rotating to the roller gaps;

the control method comprises: monitoring the real-time current of a DC drive motor through a current detection module, to adjust the rotating linear velocity of the peristaltic pump head in real time; when the peristaltic pump head is in the state of pushing a liquid to be tested, reducing the rotating linear velocity of the peristaltic pump head; and when the peristaltic pump head is in the idling state, increasing the rotating linear velocity of the peristaltic pump head.

According to some preferred aspects of the present disclosure, through respectively controlling the amount by which the rotating linear velocity of the peristaltic pump head is reduced and the amount by which the rotating linear velocity of the peristaltic pump head is increased, the amount of the liquid to be tested pushed in one rotation of the peristaltic pump head is the same before and after adjusting the rotating linear velocity of the peristaltic pump head.

According to some preferred aspects of the present disclosure, the control module is respectively connected in communication with the motor drive module, the display and the current detection module, and the display is used to display the current of the DC drive motor in real time.

According to some preferred and specific aspects of the present disclosure, in the roller gaps formed between two adjacent rollers, at least one of the roller gaps is different in size from the rest of the roller gaps.

According to some preferred implementations of the present disclosure, there is one of the roller gaps that is larger than the rest of the roller gaps.

According to some specific aspects of the present disclosure, the control method further comprises writing an operation control program for the rotational linear velocity of the peristaltic pump head within one rotation of the peristaltic pump head, and writing the operation control program into the control module.

According to some preferred aspects of the present disclosure, the control method further comprises, controlling the amount of the liquid to be tested pushed by the peristaltic pump head within one rotation of the filter membrane according to the theoretical limit pressure-bearing value of the filter membrane.

The present disclosure provides another technical solution: a sterilization method, which comprises a control method of an intelligent sterility test pump mentioned above.

The present disclosure provides another technical solution: application of the above-mentioned sterilization method in preparation or detection of foods and medicines.

Due to the use of the above technical solutions, the present disclosure has the following advantages over the prior art:

The inventors of the present disclosure have found that, during the test or detection process, the pressure pulse impact of the peristaltic pump is the main factor leading to the damage of the filter membrane, and based on this, through respectively controlling the rotational linear velocity of the peristaltic pump head at two states of the state of pushing liquid to be tested and the idling state of rotating to the roller gaps, the present disclosure prolongs the time for pushing liquid to be tested and increases the rotational linear velocity of the peristaltic pump head, effectively reduces the pressure pulse suffered by the filter membrane in the collection bottle and ensures the pushed volume and detection efficiency of the liquid to be tested. Thus, it is fundamentally ensured that the filter membrane is effectively protected during the working process, reducing the possibility of damage to the filter membrane, thereby reducing the working conditions of replacing the filter membrane and improves the detection efficiency.

wherein, 1. liquid holder; 2. support rod; 3. peristaltic pump head; 4. collection bottle holder; 5. display; 6. base; 201, roller gap; 202, roller; 203, pump shaft.

DETAILED DESCRIPTION OF EXEMPLARY EMBODIMENTS

In order to make the above objects, features and advantages of the present disclosure more apparent and easier to understand, the present disclosure will be described in detail below with reference to the accompanying drawings and specific embodiments. In the following description, numerous specific details are set forth in order to provide a thorough understanding of the present disclosure. However, the present disclosure can be implemented in many other ways different from those described herein, and those skilled in the art can make similar improvements without departing from the connotation of the present disclosure. Therefore, the present disclosure is not limited by the specific embodiments disclosed below.

The preferred embodiments of the present disclosure will be described in detail below with reference to the accompanying drawings.

Figure 1:
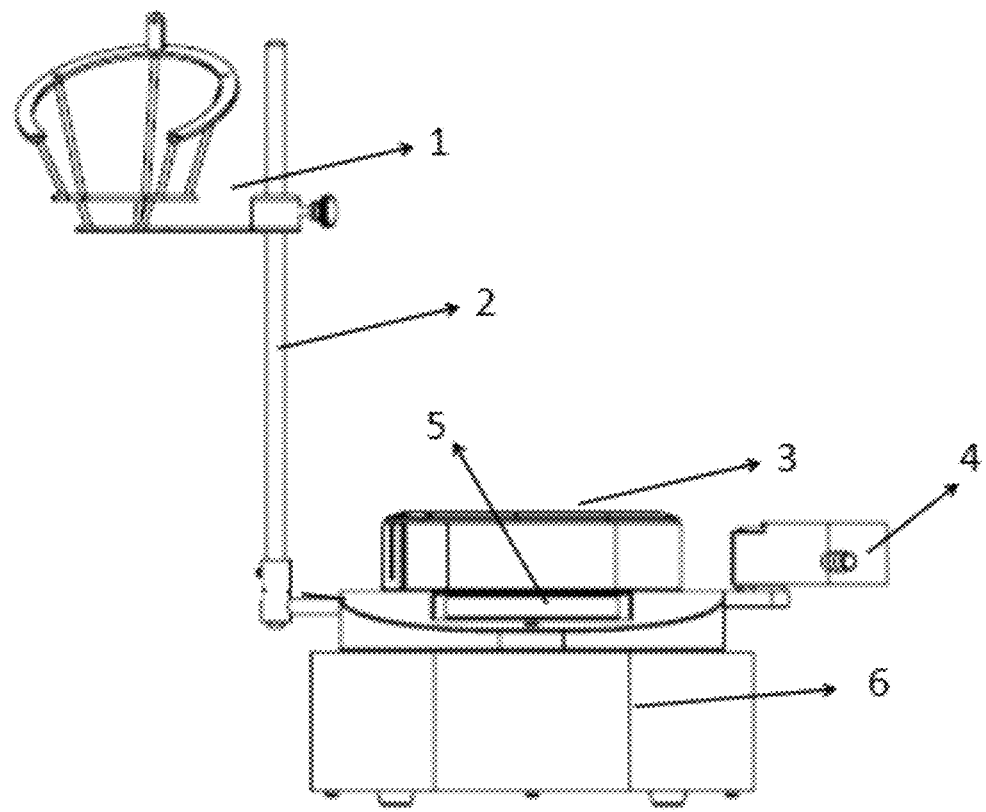
FIG. 1 is a schematic structural diagram of an intelligent sterility test pump according to an embodiment of the present disclosure.
Figure 2:
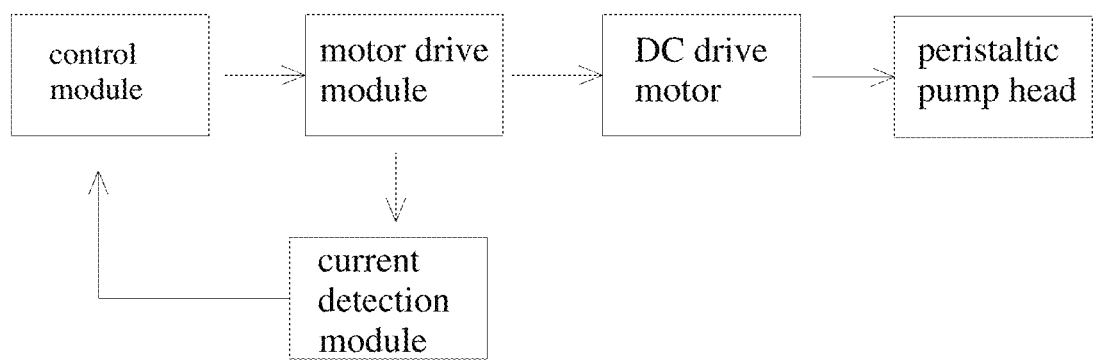
FIG. 2 is a principle schematic diagram of an intelligent sterility test pump according to an embodiment of the present disclosure.
Figure 3:
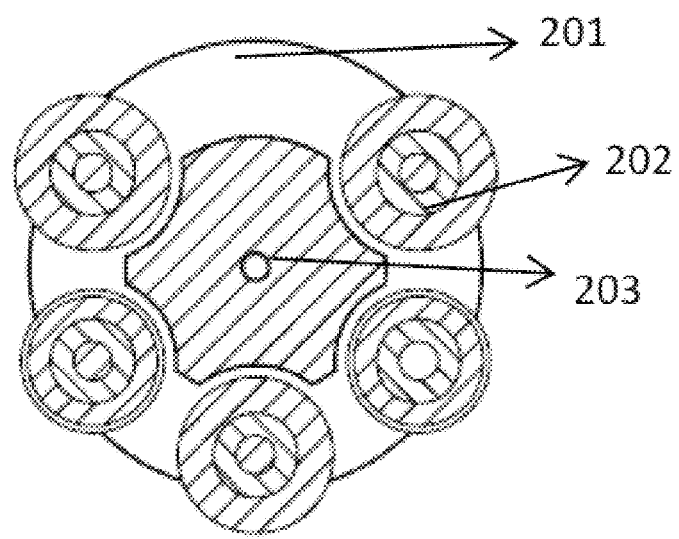
FIG. 3 is a schematic structural diagram of a peristaltic pump head according to an embodiment of the present disclosure.

As shown in FIG. 1 to FIG. 7, this embodiment provides a control method of an intelligent sterility test pump, the intelligent sterility test pump comprises a base 6, a support rod 2 arranged on the base 6, and a liquid holder 1 arranged on the upper end of the support rod 2, a peristaltic pump assembly arranged on the base 6, a collection bottle holder 4 and a display 5, the peristaltic pump assembly comprises a peristaltic pump head 3, a DC drive motor for driving the peristaltic pump head 3, a motor drive module providing current for the DC drive motor, a current detection module that detects the magnitude of the current passing through the DC drive motor, the display 5 and a control module, the peristaltic pump head 3 comprises a pump shaft 203 and a plurality of rollers 202 rotatably arranged on the pump shaft 203, and roller gaps 201 are formed between two adjacent rollers 202, specifically as shown in FIG. 1 and FIG. 3, and the basic working principle is shown in FIG. 2;

Wherein, the peristaltic pump head 3 comprises a state of pushing a liquid to be tested and an idling state of rotating to the roller gaps 201;

This control method of this embodiment comprises: monitoring the real-time current of a DC drive motor through the current detection module, to adjust the rotating linear velocity of the peristaltic pump head 3 in real time; when the peristaltic pump head 3 is in the state of pushing a liquid to be tested, reducing the rotating linear velocity of the peristaltic pump head 3; and when the peristaltic pump head 3 is in the idling state, increasing the rotating linear velocity of the peristaltic pump head 3.

In this embodiment, through respectively controlling the amount by which the rotating linear velocity of the peristaltic pump head 3 is reduced and the amount by which the rotating linear velocity of the peristaltic pump head 3 is increased, the amount of the liquid to be tested pushed in one rotation of the peristaltic pump head 3 is the same before and after adjusting the rotating linear velocity of the peristaltic pump head 3, so that the test efficiency can be guaranteed to be consistent with the original.

In this embodiment, the control module is respectively connected in communication with the motor drive module, the display 5 and the current detection module, and the display 5 is used to display the current of the DC drive motor in real time.

In this embodiment, in the roller gaps 201 formed between two adjacent rollers 202, at least one of the roller gaps 201 is different in size from the rest of the roller gaps 201. Further, there is one roller gap 201 that is larger than the rest of the roller gaps 201, as shown in FIG. 3.

In this embodiment, the control method further comprises writing an operation control program for the rotational linear velocity of the peristaltic pump head 3 within one rotation of the peristaltic pump head 3, and writing the operation control program into the control module. The modules and the method for writing programs involved in this embodiment are all in the prior art, and are specifically purchased or operated as needs, which will not be described in detail here.

In this embodiment, the control method further comprises, controlling the amount of the liquid to be tested pushed by the peristaltic pump head 3 within one rotation of the filter membrane according to the theoretical limit pressure-bearing value of the filter membrane, to ensure that the filter membrane is not damaged.

In other embodiments, a sterilization method is provided, which comprises a control method of an intelligent sterility test pump mentioned above.

In other embodiments, application of the above-mentioned sterilization method in preparation or detection of foods and medicines is provided.

Specifically, in this embodiment, as shown in FIG. 1 to FIG. 7, when the peristaltic pump DC drive motor drives the peristaltic pump head 3 to rotate, and the roller begins to squeeze the hose, and drives the liquid to be tested forward, the corresponding monitored driving current should correspond to $I_0$ at time $t_0$, and it is assumed that the rotational linear velocity of the peristaltic pump motor at this time is $v_0$, and the resistance experienced by the peristaltic pump is $F_0$, therefore:

$$F_0 \times v_0 = U \times I_0 \times \eta \quad (1)$$

wherein, U is the power supply voltage of the peristaltic pump motor, which is a constant, and $\eta$ is the efficiency of the BLDC motor.

From the roller 202 of the peristaltic pump starts to contact the hose until it pushes the liquid to be tested, under the condition that other parameters remain unchanged, its friction force is a function of the angle, namely $f(\sin \theta)$, where $\theta$ is the angle at which the roller 202 contacts the hose, so that:

$$F_0 = f(\sin \theta) + P \times S \quad (2)$$

wherein, P is the real-time pressure of the liquid in the hose, which is equal to the real-time pressure in the collection bottle, and S is the cross-sectional area of the hose.

From formulas (1) and (2), it can be obtained:

$$P = \{(U \times I_0 \times \eta)/v_0 - f(\sin \theta)\}/S \quad (3)$$

wherein, the friction force $f(\sin \theta)$ is related to the material and flatness of the surface of the hose, under certain circumstances, the value of each angle is basically constant, and a set of constant data can be obtained through actual measurement. Therefore, under the condition of constant rotation speed, the real-time pressure P in the collection bottle is proportional to the real-time load current of the peristaltic pump.

Figure 4:
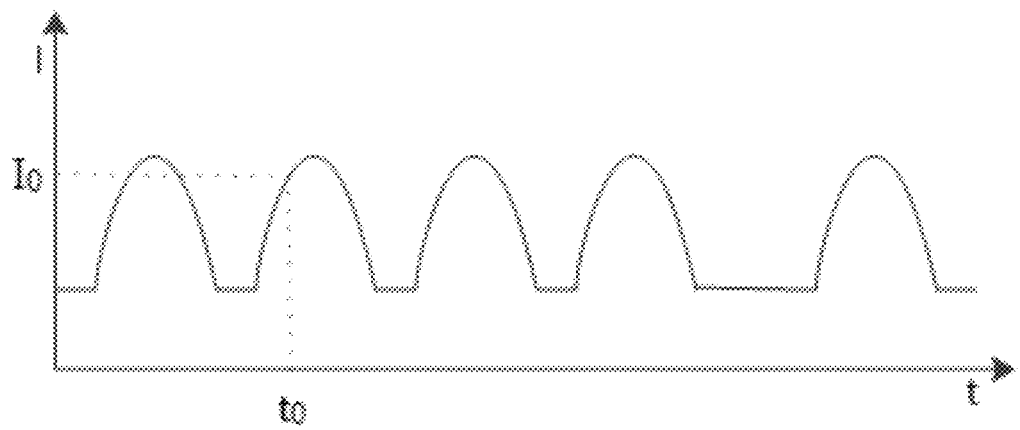
FIG. 4 is the change curve of the current over time when the intelligent sterility test pump works according to the control method in the prior art.

According to formula (3), it can be calculated that the pressure in the collection bottle is directly related to the load current of the peristaltic pump and the rotational linear velocity of the peristaltic pump. When the rotational linear velocity of the peristaltic pump is constant, if the pressure in the collection bottle increases, the monitored current of the peristaltic pump increases accordingly, that is, the current pulse shown in FIG. 4 is formed, and the pressure pulse is formed in the collection bottle as shown in FIG. 5.

Figure 5:
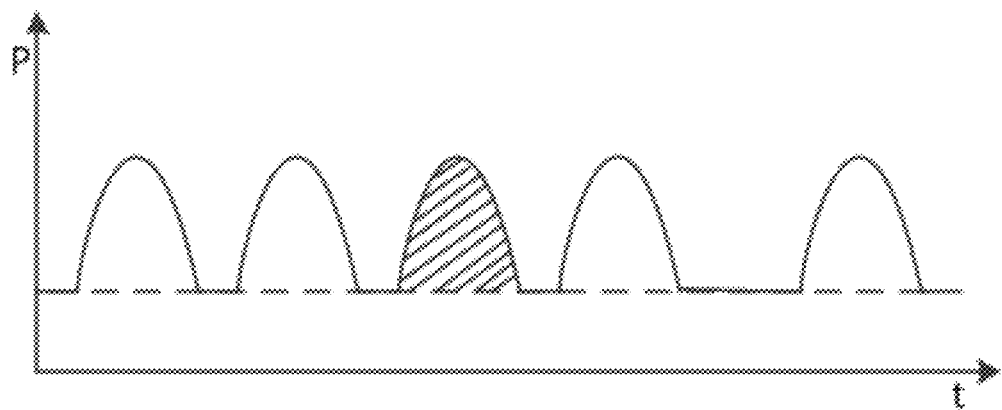
FIG. 5 is the change curve of the pressure in the collection bottle when it works according to the current mode in FIG. 4.

Assuming that the peristaltic pump can push the liquid to be tested of length L into the peristaltic pump each time, when the peristaltic pump pushes the liquid into the collection bottle, the total change of the pressure in the collection bottle can be calculated according to the ideal gas state equation as:

$$\Delta P = \{P_0(V - S \times L)\}/V \quad (4)$$

wherein, $P_0$ is the original pressure in the collection bottle, V is the volume in the collection bottle, and $\Delta P$ is the area of the shaded part in FIG. 5.

From formula (4), it can be concluded that the increased pressure $\Delta P$ mainly depends on the volume of the liquid to be tested that is pushed by the peristaltic pump each time. Under normal circumstances, the volume of the liquid to be tested that is pushed each time is basically the same, so the $\Delta P$ is basically the same, so the area of the shaded part should be the same. When the time of the shaded part is prolonged, the amplitude is greatly reduced, which effectively reduces the pressure pulse on the filter membrane in the collection bottle.

Figure 6:
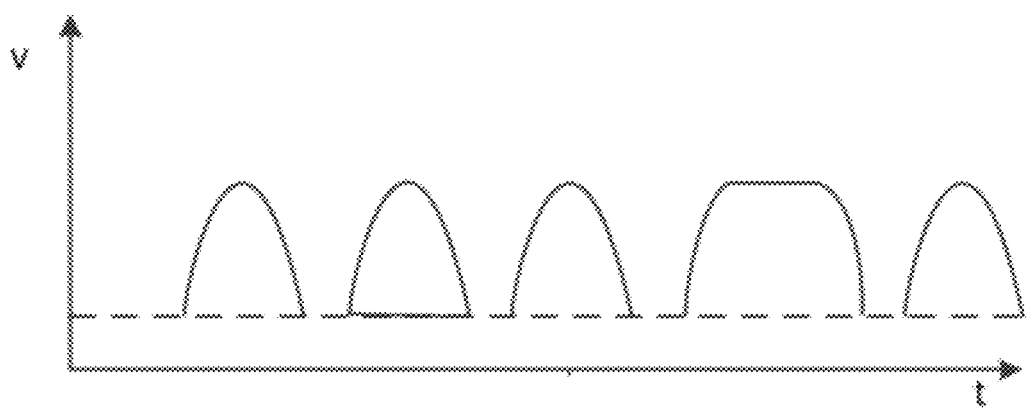
FIG. 6 is the change curve of the rotating linear velocity of the peristaltic pump head adopted by the control method of the intelligent sterility test pump according to an embodiment of the present disclosure over time.
Figure 7:
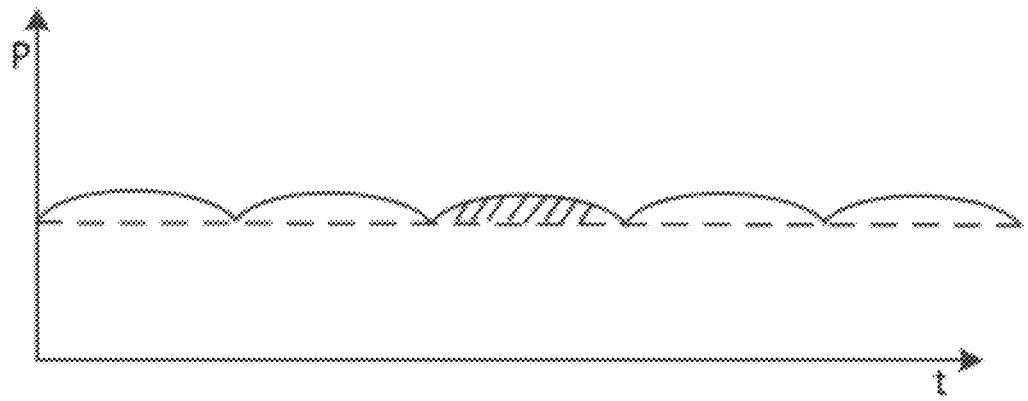
FIG. 7 is the change curve of the pressure in the collection bottle when according to the working mode shown in FIG. 6 in an embodiment of the present disclosure.

The peristaltic pump realizes the transfer of liquid into two steps: extraction and pushing, and the extraction is automatically completed when the peristaltic pump pushes the liquid. The present disclosure proposes to adjust the rotating linear velocity of the peristaltic pump head in real time by monitoring the real-time current of the peristaltic pump, and to reduce the pressure pulse amplitude in the collection bottled by prolonging the pushing time, and in order to ensure that under the condition that the flow rate of the peristaltic pump remains unchanged, the time for the peristaltic pump to rotate to the roller gaps is shorten, and the rotational linear velocity of the peristaltic pump at this time is increased, so that the time for the peristaltic pump to push the liquid once is unchanged, and the rotation speed of the peristaltic pump is adjusted as shown in FIG. 6, the pressure change in the collection bottle is shown in FIG. 7, the influence of pressure change and pressure pulse on the filter membrane is reduced, thereby prolonging the service life of the filter membrane and reducing the damage rate.

In summary, the inventor of the present disclosure has found that, during the test or detection process, the pressure pulse impact of the peristaltic pump is the main factor leading to the damage of the filter membrane, and based on this, through respectively controlling the rotational linear velocity of the peristaltic pump head at the two states, namely the state of pushing the liquid to be tested and the idling state of rotating to the roller gaps, the present disclosure prolongs the time for pushing the liquid to be tested and increases the rotational linear velocity of the peristaltic pump head, effectively reduces the pressure pulse suffered by the filter membrane in the collection bottle and ensures the pushed volume and detection efficiency of the liquid to be tested, Thus, it is fundamentally ensured that the filter membrane is effectively protected during the working process, reducing the possibility of damage to the filter membrane, thereby reducing the working conditions of replacing the filter membrane and improves the detection efficiency.

The embodiments described above are only for illustrating the technical concepts and features of the present disclosure, and are intended to make those skilled in the art being able to understand the present disclosure and thereby implement it, and should not be concluded to limit the protective scope of this disclosure. Any equivalent variations or modifications according to the essence of the present disclosure should be covered by the protective scope of the present disclosure.

The invention claimed is:

1. A control method of an intelligent sterility test pump, the intelligent sterility test pump comprising a base, a support rod arranged on the base, and a liquid holder arranged on an upper end of the support rod, a peristaltic pump assembly arranged on the base, a collection bottle holder and a display, the peristaltic pump assembly comprising a peristaltic pump head, a DC drive motor for driving the peristaltic pump head, a motor drive module providing current for the DC drive motor, a current detection module that detects magnitude of current passing through the DC drive motor, and a control module, the peristaltic pump head comprising a pump shaft and a plurality of rollers rotatably arranged on the pump shaft, roller gaps being formed between two adjacent rollers, wherein the peristaltic pump head comprises a state of pushing a liquid to be tested and an idling state of rotating to the roller gaps;

the control method comprising: monitoring real-time current of a DC drive motor through a current detection module, to adjust rotating linear velocity of the peristaltic pump head in real time; when the peristaltic pump head is in the state of pushing a liquid to be tested, reducing the rotating linear velocity of the peristaltic pump head; and when the peristaltic pump head is in the idling state, increasing the rotating linear velocity of the peristaltic pump head; and controlling the amount of the liquid to be tested pushed by the peristaltic pump head within one rotation of a filter membrane according to the theoretical limit pressure-bearing value of the filter membrane, wherein through respectively controlling amount by which the rotating linear velocity of the peristaltic pump head is reduced and amount by which the rotating linear velocity of the peristaltic pump head is increased, the amount of the liquid to be tested pushed in one rotation of the peristaltic pump head is the same before and after adjusting the rotating linear velocity of the peristaltic pump head, and wherein in the roller gaps formed between two adjacent rollers, one of the roller gaps is larger than the rest of the roller gaps.

2. The control method of an intelligent sterility test pump according to claim 1, wherein the control module is respectively connected in communication with the motor drive module, the display and the current detection module, and the display is used to display the current of the DC drive motor in real time.

3. The control method of an intelligent sterility test pump according to claim 1, wherein he control method further comprises writing an operation control program for the rotational linear velocity of the peristaltic pump head within one rotation of the peristaltic pump head, and writing the operation control program into the control module.

4. A sterilization method, wherein the sterilization method comprises the control method of an intelligent sterility test pump according to claim 1.

5. An application of a sterilization method according to claim 4 in preparation or detection of foods and medicines.

* * * * *